United States Patent
Mozdzierz (10) Patent No.: US 10,638,944 B2
(45) Date of Patent: May 5, 2020

(54) METHODS OF DETERMINING TISSUE VIABILITY

(71) Applicant: Covidien LP, Mansfield, MA (US)

(72) Inventor: Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 449 days.

(21) Appl. No.: 15/439,032

(22) Filed: Feb. 22, 2017

(65) Prior Publication Data

US 2018/0235484 A1   Aug. 23, 2018

(51) Int. Cl.
*A61B 5/026* (2006.01)
*A61B 5/022* (2006.01)
(Continued)

(52) U.S. Cl.
CPC ......... *A61B 5/0261* (2013.01); *A61B 5/0053* (2013.01); *A61B 5/0059* (2013.01); *A61B 5/0084* (2013.01); *A61B 5/015* (2013.01); *A61B 5/022* (2013.01); *A61B 5/026* (2013.01); *A61B 5/02055* (2013.01); *A61B 5/4836* (2013.01); *A61B 5/6843* (2013.01); *A61B 5/6847* (2013.01); *A61B 5/7278* (2013.01); *A61B 5/742* (2013.01); *A61B 17/29* (2013.01); *A61B 18/00* (2013.01); *A61B 34/30* (2016.02); *A61B 1/3132* (2013.01); *A61B 5/1459* (2013.01); *A61B 2017/00022* (2013.01); *A61B 2017/00057* (2013.01); *A61B 2017/00115* (2013.01); *A61B 2018/005* (2013.01); *A61B 2018/00005* (2013.01); *A61B 2018/0091* (2013.01); *A61B 2018/00184* (2013.01);
(Continued)

(58) Field of Classification Search
CPC ......... A61B 18/00; A61B 17/00; A61B 17/29; A61B 5/00; A61B 5/026; A61B 5/0261; A61B 5/6843; A61B 2018/00005; A61B 2560/0462; A61B 5/022–0235; A61B 5/02055; A61B 5/01–015
See application file for complete search history.

(56) References Cited

U.S. PATENT DOCUMENTS

| 4,109,647 A | 8/1978 | Stern et al. |
| 4,862,894 A | 9/1989 | Fujii |

(Continued)

FOREIGN PATENT DOCUMENTS

| EP | 3047805 A1 | 7/2016 |
| EP | 3181040 A1 | 6/2017 |

(Continued)

OTHER PUBLICATIONS

Mukherjee et al.,, U.S. Appl. No. 15/370,145, filed Dec. 6, 2016, entitlted Surgical Instruments Including Sensors.

(Continued)

*Primary Examiner* — Angela M Hoffa
(74) *Attorney, Agent, or Firm* — Carter, DeLuca & Farrell LLP (57) ABSTRACT

A method of performing a surgical procedure includes generating an infrared image of tissue using a thermographic camera, analyzing the infrared images to determine blood flow characteristics of the tissue, and resecting a portion of the tissue determined to have abnormal blood flow characteristics.

9 Claims, 8 Drawing Sheets

(51) Int. Cl.
  *A61B 5/0205*  (2006.01)
  *A61B 5/01*  (2006.01)
  *A61B 5/00*  (2006.01)
  *A61B 34/30*  (2016.01)
  *A61B 17/29*  (2006.01)
  *A61B 18/00*  (2006.01)
  *A61B 17/00*  (2006.01)
  *A61B 5/1459*  (2006.01)
  *A61B 90/00*  (2016.01)
  *A61B 1/313*  (2006.01)

(52) U.S. Cl.
  CPC ............ *A61B 2018/00494* (2013.01); *A61B 2018/00791* (2013.01); *A61B 2018/00863* (2013.01); *A61B 2018/00904* (2013.01); *A61B 2018/00982* (2013.01); *A61B 2090/065* (2016.02); *A61B 2505/05* (2013.01); *A61B 2560/0462* (2013.01); *A61B 2562/063* (2013.01)

(56) References Cited

U.S. PATENT DOCUMENTS

| | | | |
|---|---|---|---|
| 5,395,033 A | 3/1995 | Byrne et al. | |
| 5,445,157 A | 8/1995 | Adachi et al. | |
| 5,518,164 A | 5/1996 | Hooven | |
| 5,722,419 A | 3/1998 | Semmlow et al. | |
| 5,769,791 A | 6/1998 | Benaron et al. | |
| 7,223,279 B2 | 5/2007 | Burbank et al. | |
| 7,229,465 B2 | 6/2007 | Burbank et al. | |
| 7,618,376 B2 | 11/2009 | Kimball | |
| 8,002,795 B2 | 8/2011 | Beetel | |
| 8,073,518 B2 | 12/2011 | Chin | |
| 8,118,206 B2 | 2/2012 | Zand et al. | |
| 8,157,145 B2 | 4/2012 | Shelton, IV et al. | |
| 8,808,311 B2 | 8/2014 | Heinrich et al. | |
| 9,204,807 B2 * | 12/2015 | Leschinsky | A61B 5/015 |
| 9,204,830 B2 | 12/2015 | Zand et al. | |
| 2003/0120306 A1 | 6/2003 | Burbank et al. | |
| 2003/0139667 A1 * | 7/2003 | Hewko | A61B 5/0059 600/410 |
| 2004/0127800 A1 * | 7/2004 | Kimball | A61B 5/0261 600/483 |
| 2005/0131390 A1 | 6/2005 | Heinrich et al. | |
| 2006/0235314 A1 | 10/2006 | Migliuolo et al. | |
| 2007/0038115 A1 | 2/2007 | Quigley et al. | |
| 2009/0054908 A1 * | 2/2009 | Zand | A61B 5/0071 606/130 |
| 2009/0234248 A1 * | 9/2009 | Zand | A61B 5/0031 600/587 |
| 2010/0204698 A1 * | 8/2010 | Chapman | A61B 18/1442 606/51 |
| 2011/0144640 A1 | 6/2011 | Heinrich et al. | |
| 2011/0224518 A1 * | 9/2011 | Tindi | A61B 5/14552 600/323 |
| 2012/0123413 A1 * | 5/2012 | Chernov | A61B 18/1445 606/51 |
| 2014/0107697 A1 | 4/2014 | Patani et al. | |
| 2014/0135604 A1 | 5/2014 | Cuesta Valentin et al. | |
| 2014/0236020 A1 * | 8/2014 | Leschinsky | A61B 5/015 600/474 |
| 2014/0288386 A1 | 9/2014 | Zand et al. | |
| 2016/0073909 A1 | 3/2016 | Zand et al. | |
| 2017/0296071 A1 * | 10/2017 | Spahn | A61B 5/0261 |

FOREIGN PATENT DOCUMENTS

| | | |
|---|---|---|
| WO | 03/101277 A2 | 12/2003 |
| WO | 2007008057 A1 | 1/2007 |

OTHER PUBLICATIONS

European Search Report dated Jun. 28, 2018, corresponding to European Application No. 18157936.8; 10 pages.

* cited by examiner

METHODS OF DETERMINING TISSUE VIABILITY

BACKGROUND

1. Technical Field

The present disclosure relates to medical procedures and, more particularly, to procedures for determining and monitoring characteristics of tissue in preparation for performing various surgical procedures.

2. Background of Related Art

Colorectal surgery sometimes requires anastomosis, which involves resecting a piece of diseased bowel tissue and creating a new connection between two presumably healthy bowel segments. Typically, before performing the anastomosis, the amount of tissue to be resected is estimated using visual indicia of the bowel. The goal is to preserve as much healthy tissue as possible while at the same time removing all of the diseased tissue.

A risk involved in performing an anastomotic procedure is anastomotic leaks typically caused by a failure to resect all of the diseased tissue. Current methods used in estimating the amount of tissue to be resected during an anastomotic procedure are sometimes inadequate in preventing all anastomotic leaks. Additionally, the health and viability of colon and bowel sections may be compromised by excessive tension or insufficient blood flow in the newly attached sections.

Accordingly, a need exists for surgical instruments that can sense and visualize, either sequentially or simultaneously, a multitude of parameters and factors of the bowel tissue to aid a surgeon in performing a more successful anastomotic surgical procedure.

SUMMARY

In one aspect of the present disclosure, a method of performing a surgical procedure is provided and includes generating an infrared image of subject tissue using a thermographic camera, analyzing the infrared images to determine blood flow characteristics of the subject tissue, and resecting a portion of the subject tissue determined to have abnormal blood flow characteristics.

In some embodiments, the method may further include stapling the subject tissue upon determining that the subject tissue has normal blood flow characteristics.

In some embodiments, the method may further include comparing the infrared image of the subject tissue with an infrared image of healthy tissue to determine whether the subject tissue exhibits normal blood flow characteristics.

In some embodiments, the method may further include generating an infrared image of tissue known to be healthy using the thermographic camera, and comparing the infrared image of the tissue known to be healthy to determine whether the subject tissue exhibits normal blood flow characteristics.

In some embodiments, the thermographic camera may be a thermographic endoscope.

In another aspect of the present disclosure, a method of performing a surgical procedure is provided and includes applying pressure to a subject tissue, removing the pressure applied to the subject tissue, generating an infrared image of the subject tissue using a thermographic camera after removing the pressure applied to the subject tissue, observing a rate at which the subject tissue increases in temperature using the infrared image, and determining whether the subject tissue increases in temperature at a rate associated with healthy tissue.

In some embodiments, the method may further include resecting a portion of the subject tissue that increases in temperature at a rate associated with unhealthy tissue.

In some embodiments, the method may further include stapling the subject tissue upon determining that the subject tissue increases in temperature at the rate associated with healthy tissue.

In some embodiments, the method may further include reducing a temperature of the subject tissue prior to generating the infrared image of the subject tissue. The pressure may be applied to the subject tissue using a tissue grasper and the temperature of the subject tissue is reduced by contacting the subject tissue with pre-chilled tissue-contacting surfaces of the tissue grasper.

In yet another aspect of the present disclosure, a method of performing a surgical procedure is provided and includes determining a local perfusion pressure of subject tissue of a patient, determining a systemic blood pressure of the patient, calculating a first index using the determined local perfusion pressure and the determined systemic blood pressure, generating an infrared image of the subject tissue using a thermographic camera, analyzing the infrared image to determine blood flow characteristics of the subject tissue, and determining viability of the subject tissue based on the first index and the determined blood flow characteristics of the subject tissue.

In some embodiments, the method may further include assigning a numerical value to the tissue based on the determined blood flow characteristics, and calculating a second index using the first index and the assigned numerical value to the determine the viability of the subject tissue. The second index may be compared to a known index corresponding to viable tissue.

In some embodiments, determining the local perfusion pressure may include applying pressure to the tissue using a tissue grasper. The method may further include reducing a temperature of the subject tissue prior to generating the infrared image of the subject tissue. The temperature of the subject tissue may be reduced by contacting the subject tissue with pre-chilled tissue-contacting surfaces of the tissue grasper.

In some embodiments, the method may further include stapling the subject tissue upon determining that the subject tissue is viable.

In some embodiments, the method may further include observing a rate at which the subject tissue increases in temperature using the infrared image, and determining whether the subject tissue increases in temperature at a rate associated with healthy tissue.

In some embodiments, the method may further include comparing the infrared image of the subject tissue with an infrared image of healthy tissue to determine whether the subject tissue exhibits normal blood flow characteristics.

In some embodiments, the method may further include generating an infrared image of tissue known to be healthy using the thermographic camera, and comparing the infrared image of the tissue known to be healthy to determine whether the subject tissue exhibits normal blood flow characteristics.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Embodiments of the presently disclosed surgical systems and methods of use will now be described in detail with reference to the drawing figures wherein like reference numerals identify similar or identical elements. As used herein and as is traditional, the term "distal" will refer to that portion which is further from the clinician while the term "proximal" will refer to that portion which is closer to the clinician.

Figure 1:
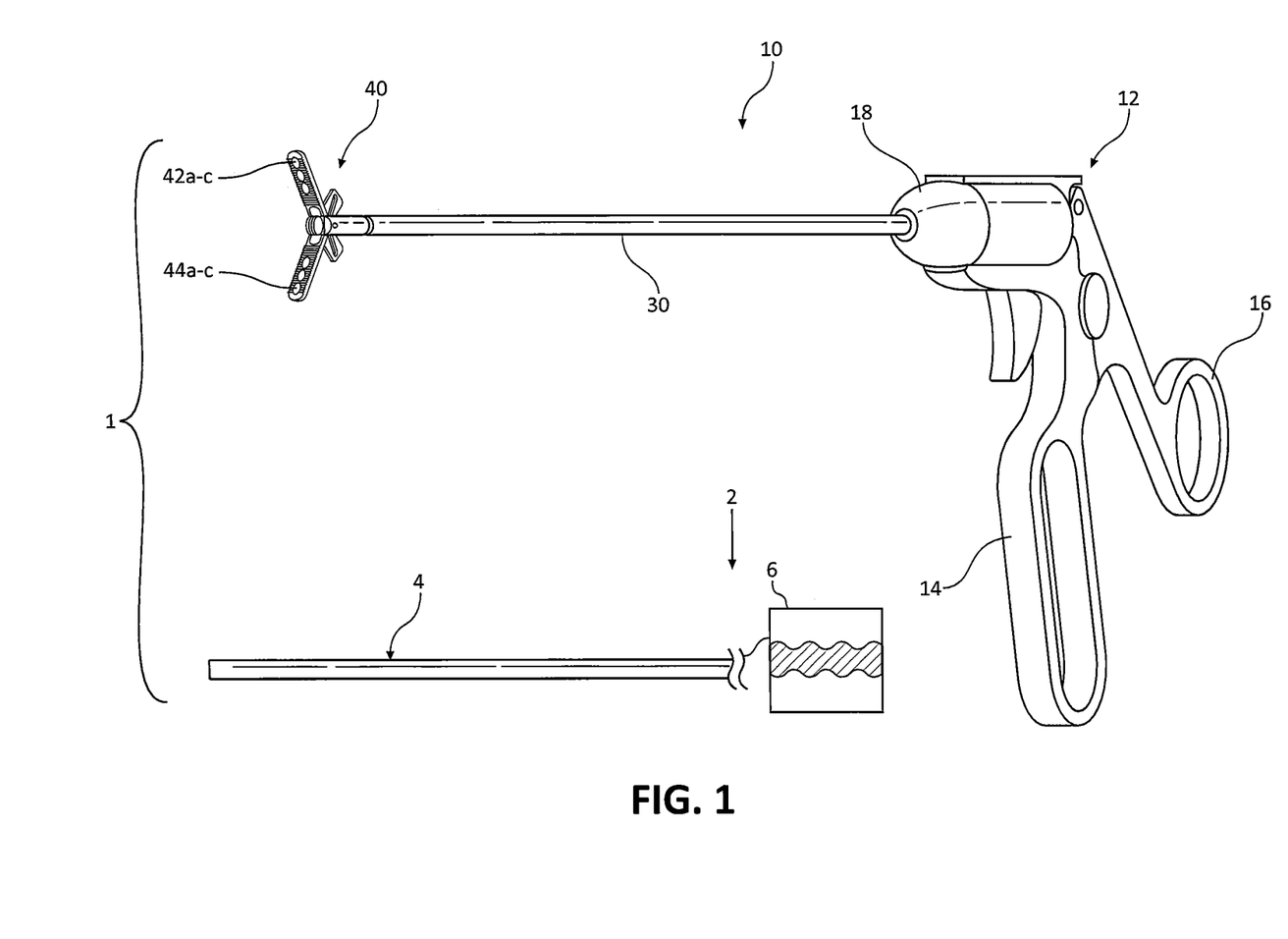
FIG. 1 is a front, perspective view of a surgical system including a surgical instrument and a thermographic camera, in accordance with the present disclosure.

With reference to FIG. 1, a medical diagnostic system 1 is illustrated, which generally includes a thermographic camera for taking infrared images of a surgical site, and a surgical instrument, such as, for example, a tissue grasper 10 for grasping and sensing a multiplicity of biological parameters of grasped tissue to assist a surgeon in performing a surgical procedure, for example, an anastomotic surgical procedure. The thermographic camera may be a thermographic endoscope 2 capable of being used in a minimally invasive manner. A detailed description of an exemplary thermographic endoscope may be found in U.S. Pat. No. 5,445,157, filed on Feb. 20, 1992, the entire contents of which are incorporated by reference herein.

The thermographic endoscope 2 includes a shaft portion 4 and a display 6 in communication (e.g., electrical or wireless) with the shaft portion 4. The shaft portion 4 is dimensioned for insertion through a surgical incision in a patient and to be positioned adjacent the tissue to be imaged. Thermographic endoscope 2 also includes an infrared image forming device (not shown) disposed in a distal portion of the shaft 4 for forming an infrared image of the tissue to be visualized, and a device (not shown) for transmitting the infrared image formed by the infrared image forming device to a device (not shown) for converting the infrared image, which is transmitted by the infrared image transmitting device into a visible image for displaying the visible image on display 6. In some embodiments, rather than using a thermographic endoscope, the surgical system 1 may utilize a portable thermographic camera not intended for use in a minimally invasive manner.

Thermographic endoscope 2 is configured to produce an image of tissue under inspection by taking advantage of the differences in the amount of infrared radiation emitted from different areas of the tissue. Different parts of tissue may exhibit unique blood flow characteristics based on various parameters of the tissue, for example, the health of the tissue (e.g., healthy, diseased, or necrosed), the amount and type of vasculature in the tissue, and the particular type of tissue (e.g., colorectal tissue). The blood flow characteristics of tissue include the rate at which tissue recovers to a baseline temperature after having been cooled to a selected temperature below the baseline temperature, and the rate at which a normal blood flow returns to the tissue after having been blocked (i.e., a perfusion rate).

As can be appreciated, due to the heat carried by blood, the blood flow characteristics of a particular tissue are closely correlated with the thermal profile exhibited by the tissue. As such, the differences in blood flow characteristics of a selected portion of tissue may be visualized using infrared imaging techniques, for example, the thermographic endoscope 2 of surgical system 1. Providing a clinician with a visual image or a live feed of infrared images of tissue (e.g., colorectal tissue) indicative of the blood flow characteristics of the tissue prior to performing an anastomosis may assist the clinician in determining whether the selected tissue is viable, as will be described in detail below.

In operation, thermographic endoscope 2 may be used prior to, during, or after a surgical procedure, for example, an anastomotic surgical procedure, to provide a clinician with enhanced visual data about the subject tissue. In an anastomotic surgical procedure, unhealthy or diseased bowel tissue is resected and the ends of the remaining healthy segments of bowel are reconnected using one of a variety of anastomosis techniques, including, but not limited to, end to end stapler anastomosis, hand sewn anastomosis, and linear stapled anastomosis. Prior to reconnecting the ends of the separate bowel segments to one another using any of the above-noted anastomosis techniques, the viability of the ends of the separate bowel segments should be assessed in order to predict the likelihood of post-surgery anastomotic leaks or other adverse outcomes. To aid in making this viability assessment, a clinician may make use of thermographic endoscope 2 of the present disclosure.

Figure 2:
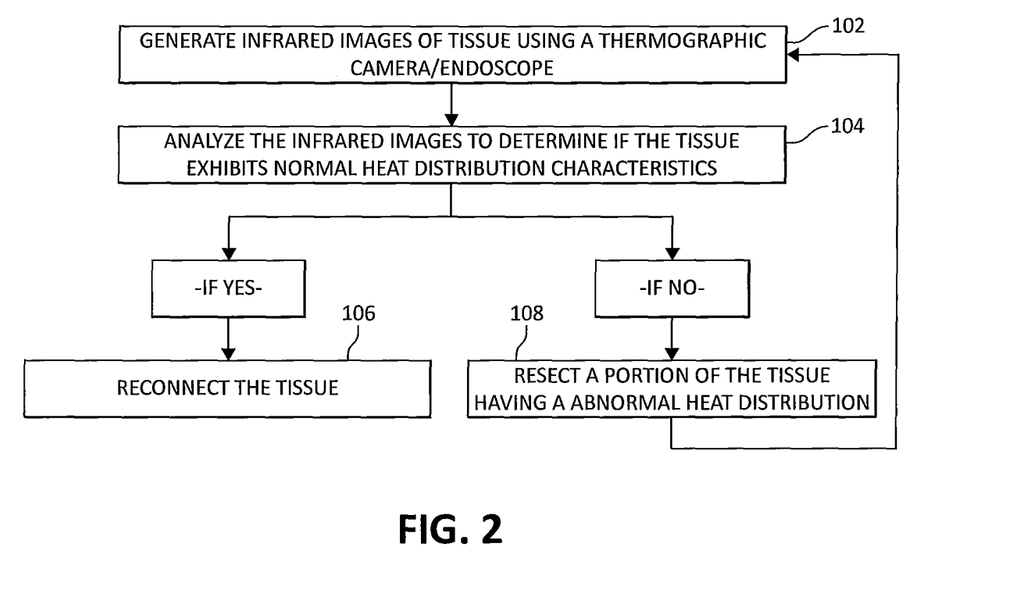
FIG. 2 is a flow chart depicting a method of using the thermographic camera of the surgical system of FIG. 1 to assess tissue viability.

With reference to FIG. 2, a use of thermographic endoscope 2 will be described. In use, each of the two ends of the presumably healthy bowel segments are imaged using the thermographic endoscope 2 by positioning the infrared image forming device (not shown) thereof adjacent the bowel segments. In step 102, the infrared image forming device forms an infrared image of the tissue, which is then converted and transmitted into a visible image or live feed of infrared images "IR" displayed on display 14. In step 104, the clinician analyzes the video feed of infrared images "IR" to determine whether the tissue exhibits normal heat distribution characteristics (e.g., a uniform heat profile throughout the imaged tissue). If the clinician determines that the tissue exhibits normal heat distribution characteristics, the clinician continues to step 106, which includes stapling the two ends of the bowel segments, thereby completing the anastomosis. Alternatively, if the clinician determines that the tissue exhibits abnormal heat distribution characteristics (e.g., a non-uniform heat profile throughout the imaged tissue), the clinician continues to step 108, which includes resecting a portion of the tissue exhibiting abnormal heat distribution characteristics. This process will have to be repeated until all of the tissue is shown to exhibit normal heat distribution characteristics.

An experienced clinician may be able to determine whether the tissue is healthy based on the infrared images "IR" alone, as described with reference to the flow chart of FIG. 2. However, with reference to FIG. 3, additional steps may be taken to assist the clinician in determining whether the subject tissue exhibits normal heat distribution characteristics.

Figure 3:
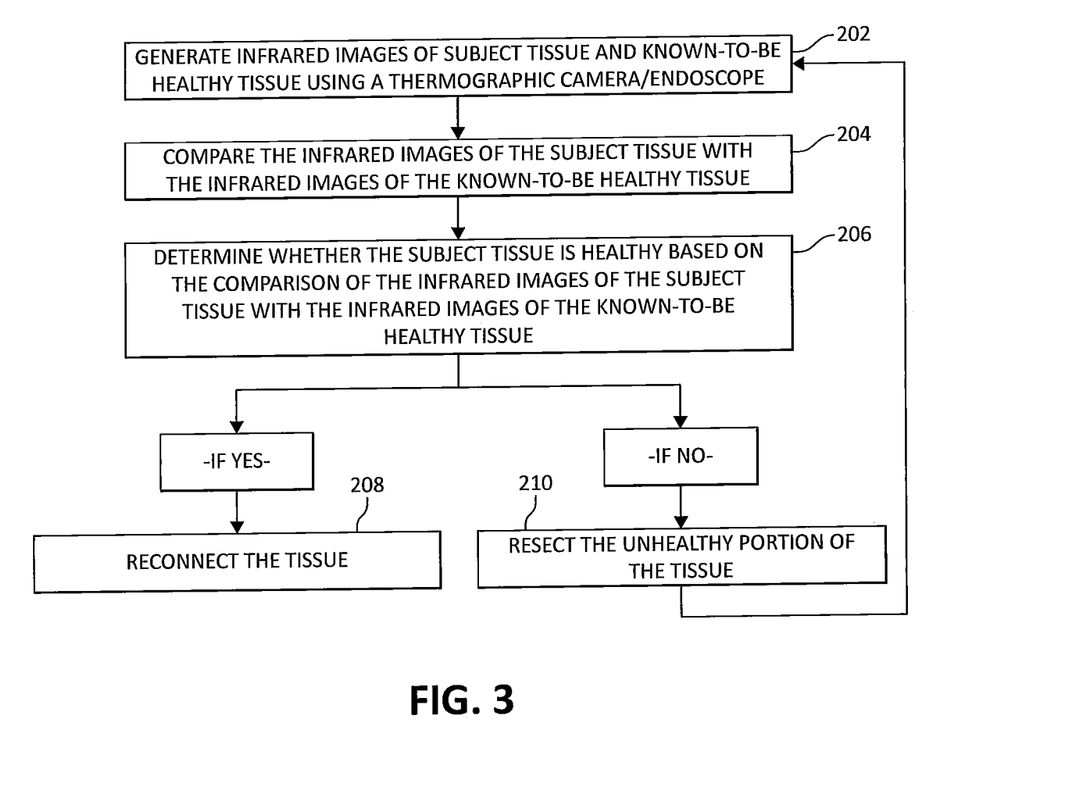
FIG. 3 is a flow chart depicting another method of using the thermographic camera of the surgical system of FIG. 1 to assess tissue viability.

In particular, in step 202, tissue that is known to be healthy may be simultaneously imaged using the thermographic endoscope 2, or in some embodiments, any suitable thermographic camera, to display infrared images of the known-to-be healthy tissue on the display 14 in juxtaposed relation to the infrared images "IR" of the subject tissue. In this way, in step 204, the clinician may compare the infrared images of the known-to-be healthy tissue and the subject tissue to determine the degree of similarity between their heat profiles. In step 206, the clinician determines whether the subject tissue is healthy based on the visual comparison of the infrared images "IR" of the subject tissue with the infrared images of the known-to-be healthy tissue.

In one embodiment, upon assessing the infrared images "R" of the subject tissue, the clinician may assign a numerical value to the subject tissue based on how close the heat distribution of the subject tissue corresponds to the heat distribution found in the known-to-be healthy tissue. For example, based on the infrared images "IR," the clinician may assign the tissue a numerical value ranging from 1 to 100, 1 to 50, 1 to 10, or 1 to 5, wherein the lowest numerical value (e.g., 1) equates to necrosed/diseased tissue, and the highest numerical value (e.g., 100) equates to ideally healthy/viable tissue. As such, a clinician can use this number, determined using the infrared images "IR" of the subject tissue, to make a determination on whether the two ends of the bowel segments are healthy enough to be reconnected or whether more tissue needs to be resected. If the clinician determines that the tissue exhibits normal heat distribution characteristics, the clinician continues to step 208, which includes reconnecting the two ends of the bowel segments, thereby completing the anastomosis. Alternatively, if the clinician determines that the tissue exhibits abnormal heat distribution characteristics compared to the known-to-be healthy tissue, the clinician continues to step 210, which includes resecting a portion of the tissue exhibiting abnormal heat distribution characteristics. This process will have to be repeated until all of the tissue is shown to exhibit normal heat distribution characteristics compared to the known-to-be healthy tissue.

Figure 4:
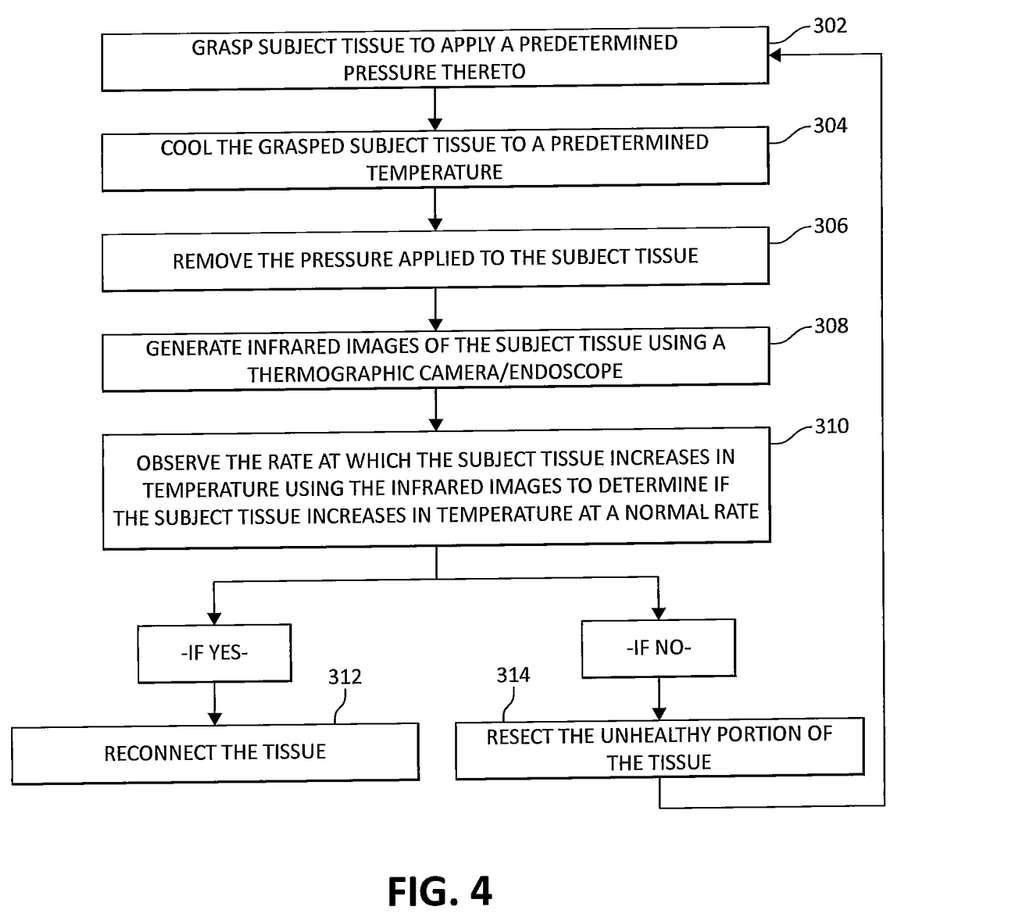
FIG. 4 is a flow chart depicting a method of using the thermographic camera in conjunction with the surgical instrument of the surgical system of FIG. 1 to assess tissue viability.

With reference to FIG. 4, manipulation of the subject tissue prior to and/or during an analysis of the infrared images "IR" of the subject tissue may further assist the clinician in gathering information about the subject tissue. For example, the infrared images "IR" generated using the thermographic endoscope 2 may be taken after performing a grasp-then-release method on the tissue to assess tissue perfusion. In particular, in step 302, the bowel segments may be grasped, either separately or together, using any suitable device (e.g., tissue grasper 10) capable of applying a clamping pressure on the tissue sufficient to prevent or substantially prevent blood from flowing through the grasped tissue. Clamping the tissue in this way removes a substantial amount of blood from each of the two ends of bowel segments, thereby bringing each portion of the subject tissue to the substantially same temperature, in effect calibrating the tissue. In step 304, in the instance where tissue grasper 10 is used to clamp the tissue, the tissue may be cooled by pre-chilling the tissue-contacting surfaces 54, 56 of tissue grasper 10 and grasping the tissue between the pre-chilled tissue contacting-surfaces 54, 56 of tissue grasper 10.

Upon the ceasing of blood flow through the grasped tissue and/or the cooling of the grasped tissue from the pre-chilled tissue-contacting surfaces 54, 56 of tissue grasper 10, thermographic endoscope 2 is positioned so that the infrared image forming device of thermographic endoscope 2 is facing the grasped tissue. In step 306, the clamping pressure on the tissue is removed to allow for blood flow to return to the tissue to gradually restore the temperature of the tissue to its initial value or baseline temperature. This grasp-and-release step allows for a more accurate determination of the heat profile of the subject tissue.

In step 308, a video feed of infrared images taken by thermographic endoscope 2 of the subject tissue will be displayed on display 14 beginning at the time the clamping pressure on the tissue is released. As the blood begins to return to the tissue, the amount of infrared radiation emitted by the tissue will increase at a rate correlated with the health of the tissue. For example, if the tissue is healthy, tissue perfusion should occur at a rate that is known for healthy tissue of the type being studied. Accordingly, the infrared images "IR" taken by thermographic endoscope 2 would indicate that the tissue increased in temperature (due to blood flowing therethrough) at a rate substantially similar or the same as that known for healthy tissue. Alternatively, if the tissue is not healthy or not viable, tissue perfusion should occur at a rate less than expected for otherwise healthy tissue of the particular type being studied. Accordingly, the infrared images "IR" taken by thermographic endoscope 2 would indicate that the tissue increased in temperature (due to blood flowing therethrough) at a rate less than that known for otherwise healthy tissue. As such, in step 310, the clinician visually observes the rate at which the subject tissue increases in temperature using the infrared images "IR" to determine whether the subject tissue increases in temperature at a normal rate.

An experienced clinician may be able to determine whether the tissue is healthy based solely on the rate of thermal change of the tissue visually observed from the infrared images "IR" However, to assist the clinician in determining whether the subject tissue exhibits a normal rate of thermal change, a measurement may be taken of the time it takes for the tissue to return to its initial, baseline temperature. This measured time may be compared to an index containing a list of known times each corresponding to a different degree of viability of tissue of the type being studied. For example, if healthy bowel tissue is known to typically take approximately 5 seconds to warm up naturally to its baseline temperature after being chilled to 5 degrees Fahrenheit below its baseline temperature, and the bowel tissue being studied was measured to take approximately 10 seconds, this information can be used by the clinician to determine that the subject tissue may not be viable. As such, a clinician can use this information, determined using the infrared images "IR" of the subject tissue, to make a determination on whether the two ends of the bowel segments are healthy enough to be reconnected or whether more tissue needs to be resected. If the clinician determines that the tissue returns to its baseline temperature at a normal rate, the clinician continues to step 312, which includes stapling the two ends of the bowel segments, thereby completing the anastomosis. Alternatively, if the clinician determines that the tissue returns to its baseline temperature at an abnormal rate (e.g., faster or slower than that expected), the clinician continues to step 314, which includes resecting a portion of the tissue exhibiting an abnormal rate of thermal change. This process will have to be repeated until all of the tissue is shown to exhibit normal rates of thermal change.

As will be described below, the above-described methods of using thermographic imaging to assess tissue viability may be used in combination with other measurements taken of the patient, for example, a local perfusion pressure reading and/or a systemic blood pressure reading, to provide an even more accurate assessment of tissue viability.

With reference to FIGS. 1A and 5-10, surgical system 1 may further include tissue grasper 10, which is configured to grasp tissue and sense a multiplicity of biological parameters of the grasped tissue to assist a surgeon in performing a surgical procedure, for example, an anastomotic surgical procedure. The tissue grasper 10 generally includes a handle portion 12, an elongated shaft 30, and a jaw assembly 40.

Figure 5:
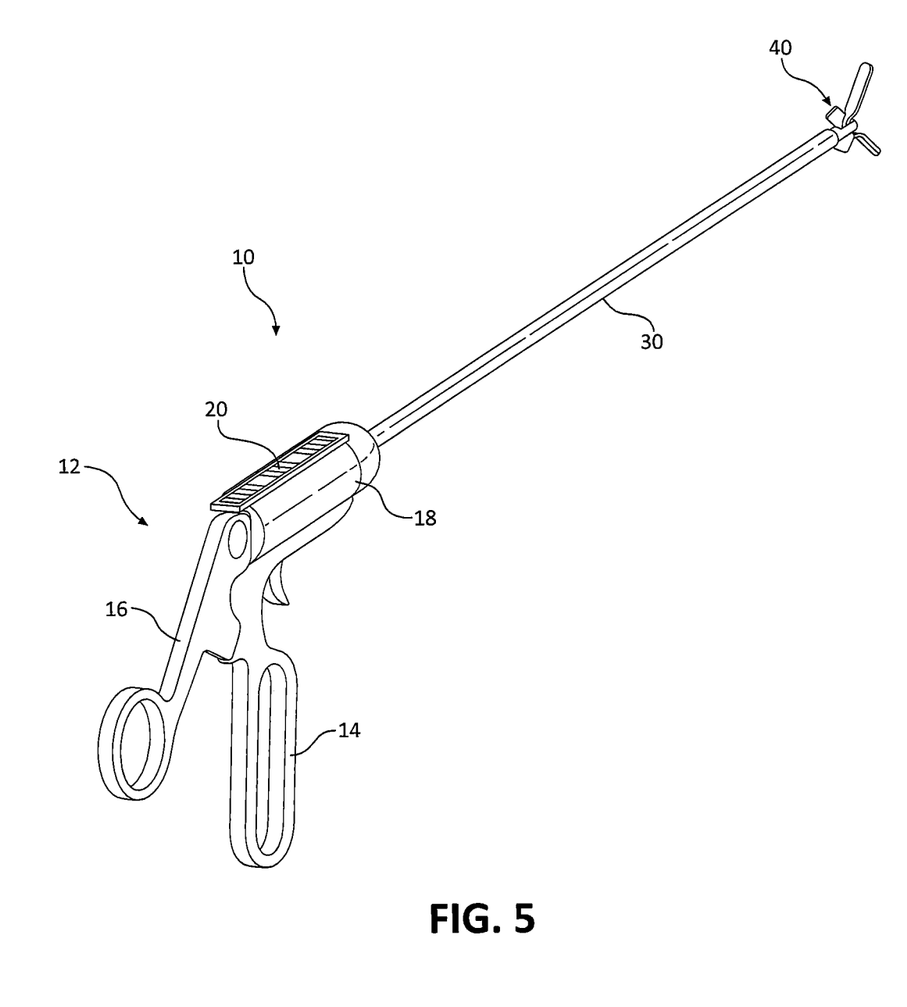
FIG. 5 is a rear, perspective view of the surgical instrument of the surgical system of FIG. 1.

The handle portion 12 of the tissue grasper 10 includes a stationary handle 14 and a pivoting or movable handle 16 pivotably coupled to the stationary handle 14. Manipulation of the pivoting handle 16 relative to the stationary handle 14 effects a closing of the jaw assembly 40 to grasp tissue. The handle portion 12 of the tissue grasper 10 includes a longitudinal body portion 18 formed with the stationary handle 14. The body portion 18 has a display 20, for example, an LED display or liquid-crystal display ("LCD") for displaying various tissue parameters measured by various sensors 42*a-c*, 44*a-c* of the tissue grasper 10.

Figure 6:
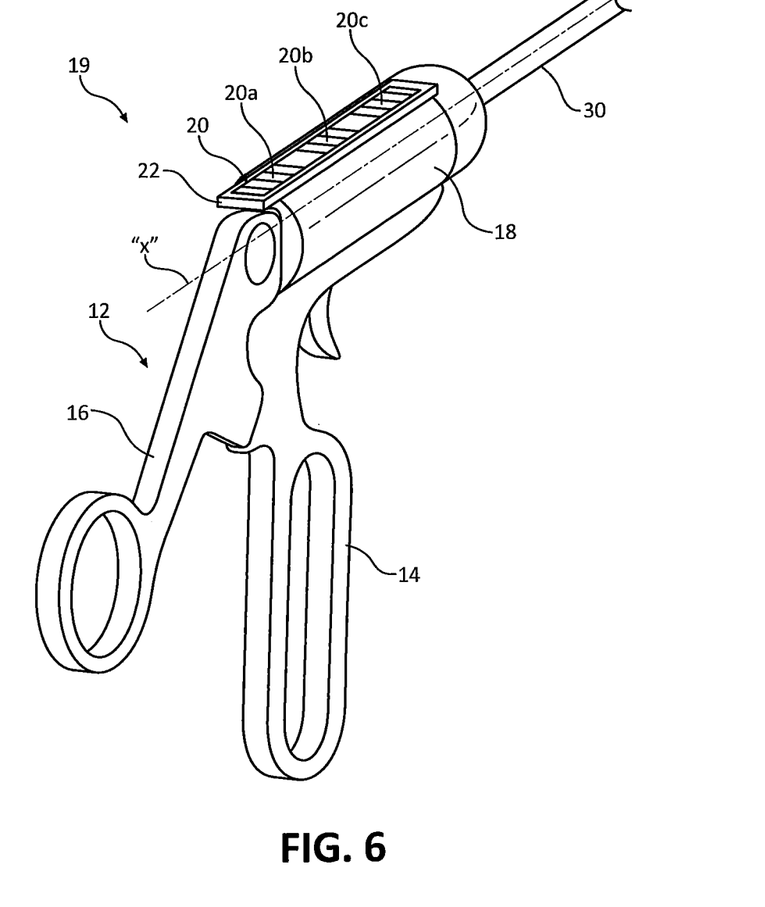
FIG. 6 is an enlarged view of a handle portion of the surgical instrument of FIG. 5 illustrating a display of the surgical instrument.
Figure 7:
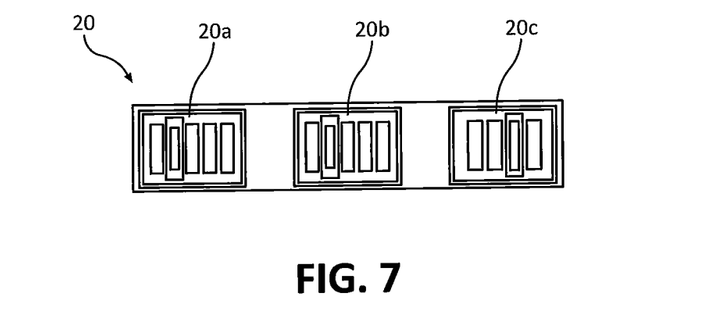
FIG. 7 is an enlarged view of the display of the surgical instrument of FIG. 5.

With reference to FIGS. 6 and 7, the body portion 18 of the handle portion 12 defines a longitudinal axis "X" that is coaxial with a longitudinal axis defined by the elongated shaft 30. The body portion 18 has a planar upper surface 22 on which the display 20 is situated. It is contemplated that the display 20 may be disposed at any suitable location of the body portion 18 or on any other component of the tissue grasper 10.

The display 20 may have multiple display sections, for example, three display sections 20*a*, 20*b*, 20*c*, arranged in a linear array along the longitudinal axis "X." It is contemplated that the display 20 may include more or less than three discrete display sections. A first display section 20*a* of the display 20 is configured to display a visual indication of a measured tissue perfusion of tissue grasped by the tissue grasper 10. A second display section 20*b* of the display 20 is configured to display a visual indication of a measured amount of pressure being applied to tissue grasped by the tissue grasper 10. A third display section 20*c* of the display 20 is configured to display a measured thickness of the tissue grasped by the tissue grasper 10.

The visual indication displayed by each of the display sections 20*a*, 20*b*, 20*c* includes a range of colors increasing in brightness from a proximal portion to a distal portion thereof. For example, when viewing each of the first and second display sections 20*a*, 20*b* in a proximal to distal direction, the first and second display sections 20*a*, 20*b* may each be green, yellow, orange, and then red, with each color portion gradually blending into the adjacent color portion. Other colors and color arrangements for the first and second display sections 20*a*, 20*b* are contemplated. The tissue grasper 10 may be configured such that when the green of the first display section 20*a* is lit, this may indicate a relatively high tissue perfusion being measured by the tissue grasper 10, whereas when the red of the first display section 20*a* is lit, this may indicate a relatively low tissue perfusion being measured by the tissue grasper 10. The information related to the tissue perfusion may be useful when making a determination on the viability of the tissue being grasped, as will be described in more detail below.

With reference to the second display section 20*b* of the display 20, when the green of the second display section 20*b* is lit, this may be indicative of a relatively low grasping or clamping pressure being applied to tissue by the tissue grasper 10, whereas when the red of the second display section 20*b* is lit, this may be indicative of a relatively high grasping or clamping pressure being applied to tissue by the tissue grasper 10. The clamping pressure measured by the tissue grasper 10 and displayed by the second display section 20*b* of the tissue grasper 10 is used in conjunction with the tissue perfusion displayed by the first display section 20*a* of the tissue grasper 10 to determine the perfusion pressure of the grasped tissue.

The perfusion pressure is measured by applying a sufficient amount of clamping pressure on the subject tissue until there is no perfusion (i.e., no blood flow) through the tissue, and then slowly reducing the clamping pressure until perfusion through the grasped tissue restarts. The pressure at which the perfusion restarts is the tissue perfusion pressure. For a detailed description of a method of measuring surface perfusion pressure, reference may be made to U.S. Pat. No. 7,618,376, the entire contents of which are incorporated by reference herein.

The information related to the amount of pressure being applied to tissue by the tissue grasper 10 may also be useful in preventing over-compression of tissue to prevent damage to healthy tissue.

In viewing the third display section 20*c* from a proximal to distal direction, the third display section 20*c* may be grey, brown, violet, and black. In some embodiments, third display section 20*c* may be grey, white, blue, purple, tan, green, and black. Other colors and color arrangements for the third display section 20*c* are contemplated. When the grey (proximal portion) of the third display section 20*c* is lit, this may be an indication that tissue grasped by the tissue grasper 10 has a relatively small thickness (i.e., the tissue is too thin to withstand being reconnected), whereas when the black (distal portion) of the third display section 20*c* is lit, this may be an indication that tissue grasped by the tissue grasper 10 has a relatively large thickness (i.e., the tissue is too thick to be reconnected). The information related to tissue thickness may be useful for making a determination on the type of reconnection technique to be used. Where stapling is selected, the information can be useful in selecting the size of the staples to be used when performing a surgical anastomosis on the grasped tissue.

In some embodiments, instead of display 20 utilizing ranges of colors or brightness to illustrate the measured tissue parameters (e.g., tissue perfusion, tissue compression, and tissue thickness), the display 20 may display ranges of numbers or various numeral outputs. In particular, the first, second, and third display sections 20*a*, 20*b*, 20*c* may display the number ranges 0 to 3, 0 to 5, 0 to 10, 0 to 100, or any other suitable range, to illustrate information about the tissue being grasped by the tissue grasper 10. For example, when the first display section 20*a* displays the number 0, this may be an indication that the grasped tissue has very little or no perfusion (i.e., no blood flow), whereas when the first display section 20a displays the number 100, this may be an indication that the grasped tissue has a high perfusion (i.e., ideal blood flow).

In some embodiments, the display 20 may illustrate information about grasped tissue utilizing any suitable indicia, for example, words such as poor, satisfactory, or good.

In some embodiments, tissue grasper 10 may not include display 20, and instead, tissue grasper 10 may be configured to be connected to or be in communication with another type of display, for example, display 6 of thermographic endoscope 2, a tablet, a cell phone, a computer monitor, a laptop, or any suitable display device. Tissue grasper 10 may be connected to any of the aforementioned display devices via USB wires, Wi-Fi, or the like.

Figure 8:
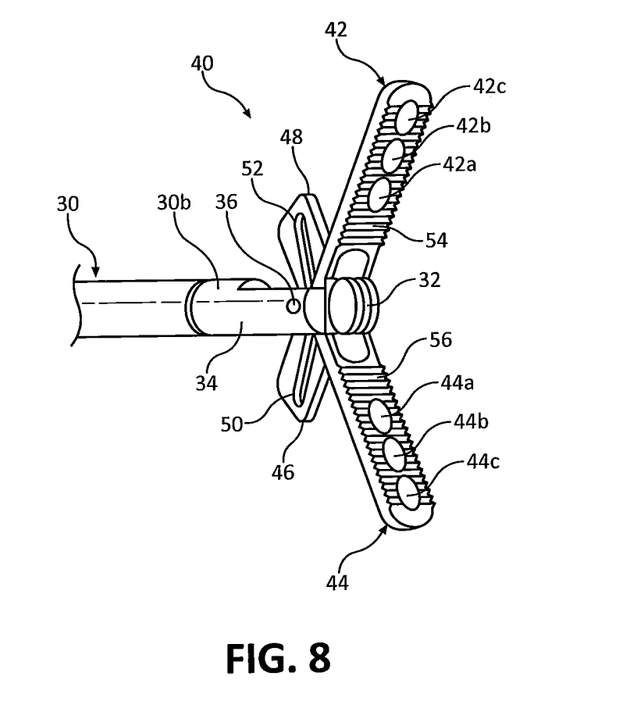
FIG. 8 is an enlarged view of a jaw assembly of the surgical instrument of FIG. 5 illustrating sensors incorporated therein.

With reference to FIGS. 1, 5, and 8, the elongated shaft 30 of tissue grasper 10 extends distally from the handle portion 12 and houses an actuation rod (not explicitly shown). The elongated shaft 30 may be rotatable with respect to the handle portion 12 to rotate the jaw assembly 40 about the longitudinal axis "X." The elongated shaft 30 has two prongs 32, 34 formed at its distal end 30b. A pivot pin 36 extends transversely through the prongs 32, 34 and the jaw assembly 40 to provide a point about which the jaw members 42, 44 of the jaw assembly 40 pivot. The actuation rod has a proximal end (not shown) operably coupled to the movable trigger 16 (FIGS. 1, 5), and a distal end (not shown) extending between the prongs 32, 34 and which is operably coupled to the jaw assembly 40.

Figure 9:
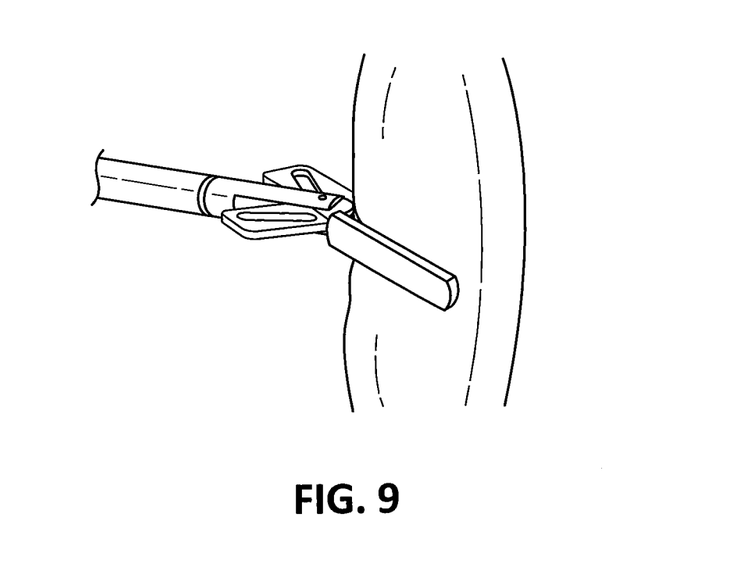
FIG. 9 is a top view of the surgical instrument of FIG. 5 illustrating the jaw assembly grasping tissue.

With reference to FIGS. 8 and 9, the jaw assembly 40 includes first and second juxtaposed jaw members 42, 44, respectively, which are simultaneously movable between a substantially approximated position, in which the jaw members 42, 44 are in relatively close relation to one another, and a spaced position, in which the jaw members 42, 44 are separated at least a sufficient distance to receive tissue therebetween, for example, tissue "T." The jaw assembly 40 includes a first proximal portion or a first flange 46 extending proximally from the first jaw member 42, and a second proximal portion or a second flange 48 extending proximally from the second jaw member 44. The flanges 46, 48 each include an elongated angled cam slot 50, 52 defined therethrough configured to engage the distal end of the actuation rod (not explicitly shown) that drives the opening and closing of the jaw members 42, 44 as the actuation rod moves through the cam slots 50, 52. As such, manipulation of the pivoting handle 16 (FIGS. 1, 5) relative to the stationary handle 14 actuates the actuation rod to effect an opening or a closing of the jaw assembly 40 about tissue "T."

With continued reference to FIGS. 8 and 9, the jaw members 42, 44 each have a tissue contacting surface 54, 56 such that when the jaw assembly 40 is in the closed configuration, tissue "T" is grasped between the tissue contacting surfaces 54, 56. The jaw assembly 40 may be coupled to a cooling system (not shown) configured to pass coolant through jaw member 42, 44 to cool tissue contacting surfaces 54, 56 thereof. Alternatively, tissue contacting surfaces 54, 56 may include a thermoelectric cold plate for reducing the temperature of tissue contacting surfaces 54, 56. Tissue contacting surfaces 54, 56 are cooled so that when tissue contacting surfaces 54, 56 are applied to tissue, the tissue contacting surfaces 54, 56 reduce the temperature of the tissue, as will be described in detail below.

The jaw members 42, 44 each have a first sensor 42a, 44a, a second sensor 42b, 44b, and a third sensor 42c, 44c, disposed on respective tissue contacting surfaces 54, 56. The sensors 42a-c, 44a-c are arranged on respective tissue contacting surfaces 54, 56 in a linear array along a longitudinal axis defined by respective jaw members 42, 44. In some embodiments, the sensors 42a-c, 44a-c may be arranged on respective tissue contacting surfaces 54, 56 in any suitable manner.

The first sensors 42a, 44a of the jaw assembly 40 are perfusion sensors, for example, Doppler flow sensors, configured to measure local perfusion (i.e., blood flow) through tissue grasped between the jaw members 42, 44. The first sensors 42a, 44a may measure perfusion of the grasped tissue on the basis of known techniques, such as Laser-Doppler Flowmetry ("LDF"), measuring light scattering, and/or measuring absorption of light from one or more LED's or other light sources. For a detailed description of LDF technology, reference may be made to U.S. Pat. Nos. 4,109,647 and 4,862,894, the entire contents of each of which are incorporated by reference herein.

In some embodiments, only one of the tissue contacting surfaces 54, 56 of the jaw assembly 40 has a perfusion sensor. The first sensors 42a, 44a are in communication, via lead wires or wireless connection, with the first display section 20a of the display 20 such that upon the first sensors 42a, 44a measuring the perfusion in grasped tissue, the first sensors 42a, 44a transmit the measurement data to the first display section 20a, which displays the measurement in any of the manners described above with reference to FIGS. 2 and 3 (e.g., a range of colors, brightness levels, numbers, words.)

In some embodiments, the first sensors 42a, 44a may also be in communication, via lead wires or wireless connection, with a computing device or processor (not shown) such as a laser Doppler monitor, which processes the information collected by the first sensors 42a, 44a to calculate the tissue perfusion. The computing device may also be in communication, via lead wires or wireless connection, with the first display section 20a to send the processed information related to the tissue perfusion to the first display section 20a so that the first display section 20a can display the tissue perfusion in any of the manners described above with reference to FIGS. 6 and 7 (e.g., colors, brightness levels, numbers, words.)

With continued reference to FIGS. 8 and 9, the second sensors 42b, 44b of the jaw assembly 40 are pressure sensors or pressure measuring devices, for example, MEMS devices. For a detailed description of various MEMS devices, reference may be made to U.S. Pat. No. 8,808,311, the entire contents of which are incorporated by reference herein. The second sensors 42b, 44b are configured to measure the amount of pressure applied by the tissue grasper 10 to the grasped tissue (i.e., the clamping pressure). In some embodiments, only one of the tissue contacting surfaces 54, 56 has a pressure sensor. The second sensors 42h, 44h are in electrical communication, via lead wires of wireless connection, with the second display section 20h of the display 20 such that upon the second sensors 42b, 44b measuring the clamping pressure applied to the grasped tissue, the second sensors 42b, 44b transmit the measurement data to the second display section 20b, which displays the measurement in any of the manners described above with reference to FIGS. 6 and 7 (e.g., colors, brightness levels, numbers, words.) Additionally or alternately, the second sensors 42b, 44b may send the measured clamping pressure to the computing device for processing, which then sends the information to the display 20.

The third sensors 42c, 44c of the jaw assembly 40 are gap determination elements, for example, slide potentiometers, rotational potentiometers, devices used to measure impedance between the contacting surfaces 54, 56, or Linear Variable Differential Transformers ("LVDT"), configured to measure the thickness of the grasped tissue by measuring the gap distance between the jaw members 42, 44. For a detailed description of various sensors capable of measuring tissue thickness, reference may be made to U.S. Pat. No. 8,002,795, the entire contents of which are incorporated by reference herein. In some embodiments, only one of the tissue contacting surfaces 54, 56 has a gap determination element. The third sensors 42c, 44c are in electrical communication, via wire leads or wireless connection, with the third display section 20c of the display 20 such that upon the third sensors 42c, 44c measuring the tissue thickness of the grasped tissue, the third sensors 42c, 44c transmit the measurement data to the third display section 20c, which displays the measurement in any of the manners described above with reference to FIGS. 6 and 7 (e.g., colors, brightness levels, numbers, words.) Additionally or alternately, the third sensors 42c, 44c may be in communication, via lead wires or wireless connection, to the computing device, which receives the tissue thickness measurements from the third sensors 42c, 44c, and processes the measurement data and then sends the information to the display 20.

In some embodiments, the display 20 may include a fourth display section (not shown) configured to display an index representative of the ratio of the surface perfusion pressure measured by first sensors 42a, 44a and second sensors 42b, 44b of the tissue grasper 10, and a systemic blood pressure measured by a blood pressure cuff (not shown), as will be described in detail below.

In operation, the tissue grasper 10 may be used prior to, during, or after a surgical procedure, for example, an anastomotic surgical procedure, to gather various data about the subject tissue. In an anastomotic surgical procedure, unhealthy or diseased bowel tissue is resected and the ends of the remaining healthy segments of bowel are reconnected. Prior to reconnecting the ends of the separate bowel segments to one another, the viability of the ends of the separate bowel segments should be assessed in order to predict the likelihood of post-surgery anastomotic leaks or other adverse outcomes. To aid in making this viability assessment, a surgeon may make use of the tissue grasper 10 in conjunction with the thermographic endoscope 2 (FIG. 1).

In use of the tissue grasper 10, each of the two ends of the presumably healthy bowel segments are grasped, either separately or together, between the tissue contacting surfaces 54, 56 of the jaw assembly 40. While monitoring the perfusion reading (i.e., blood flow) displayed on the first display section 20a of the tissue grasper 10, the pivoting handle 16 is manipulated to gradually increase the clamping pressure until the perfusion reading indicates that no blood flow or virtually no blood flow is moving through the grasped tissue. While continuously monitoring both the first and second display sections 20a, 20b, the movable handle 16 of the tissue grasper 10 is manipulated to gradually reduce the amount of clamping pressure being applied to the tissue. The clamping pressure is reduced until first display section 20a displays a perfusion reading indicating that blood flow has returned to the grasped tissue. At the moment that the perfusion reading indicates that the blood flow is returned, the clamping pressure reading displayed by the second display section 20b is noted, which is the local perfusion pressure of the grasped tissue. The measured local perfusion pressure may be used to assess the viability of the grasped tissue. Additionally or alternately, the measured local perfusion pressure may be used in combination with other measurements and observations, for example, a systemic blood pressure reading and infrared images of the tissue, to aid in making the determination of the viability of the tissue.

Figure 10:
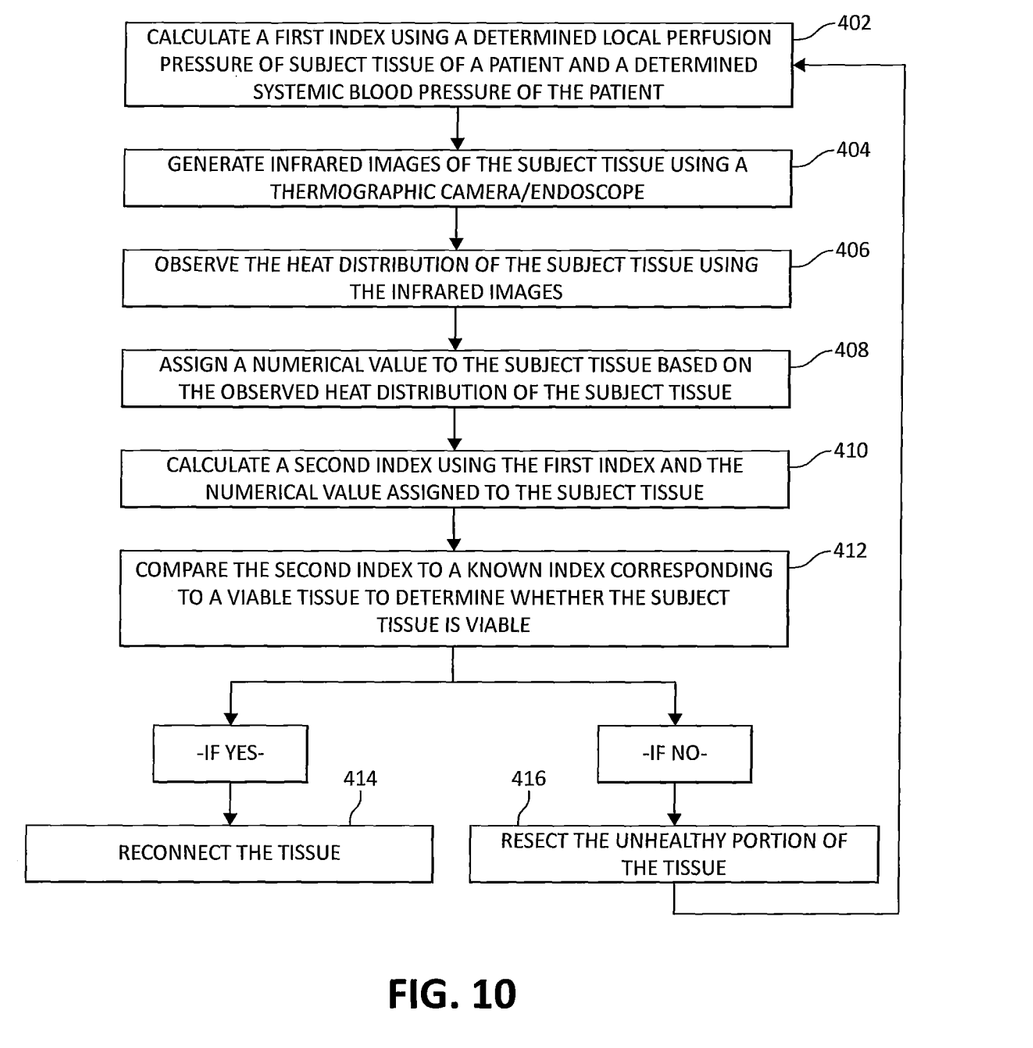
FIG. 10 is a flow chart depicting another method of using the thermographic camera of FIG. 1 in conjunction with the surgical instrument of FIG. 5 to assess tissue viability.

The systemic blood pressure may be taken using any suitable device, for example, a blood pressure cuff, applied to any suitable body portion of the patient, for example, the arm of the patient. With reference to FIG. 10, in step 402, an index may be calculated by taking a ratio of the local perfusion pressure measured by the tissue grasper 10 and the systemic blood pressure taken using the blood pressure cuff. The index may be calculated by the computing device and displayed as a number on the display 20 of the tissue grasper 10. The calculated index is predictive of whether an anastomotic leak may occur and/or the grade of an anastomotic leak. As such, a surgeon can use the index to make a determination on whether the two ends of the presumed healthy bowel segments are healthy enough to be reconnected or whether more tissue needs to be resected. For a detailed description of a method of calculating a perfusion index, reference may be made to U.S. Pat. No. 7,618,376, the entire contents of which were incorporated by reference above.

To provide a more precise assessment of tissue viability, the thermographic endoscope 2 may be used in conjunction with the measurements taken by the tissue grasper 10 and the blood pressure cuff. In step 404, infrared images of the subject tissue are generated using thermographic endoscope 2 and in step 406, the infrared images of the subject tissue are analyzed to observe the heat distribution characteristics of the subject tissue. In some embodiments, prior to step 404, tissue grasper 10 may be used to initiate the grasp-then-release steps 302, 304, 306 of FIG. 4. In step 408, the tissue may be assigned a numerical value by the clinician based on the heat distribution characteristics observed using the infrared images of the subject tissue displayed on display 6. In step 410, this numerical value may be compared with the local perfusion pressure/systemic blood pressure index to provide a second index. In step 412, this second index may be compared to a known index corresponding to viable tissue to determine whether the tissue is viable. If the calculated second index is the same or substantially the same as the known index corresponding to viable tissue, the clinician continues to step 414, which includes reconnecting the two ends of the bowel segments, thereby completing the anastomosis. Alternatively, if the calculated second index deviates a threshold amount from the known index corresponding to viable tissue, the clinician continues to step 416, which includes resecting more of the tissue. This process will have to be repeated until all of the tissue is determined to be viable.

In some embodiments, the tissue grasper 10 may be pre-programmed to clamp tissue at a predetermined clamping pressure that is known to result in perfusion through the grasped tissue to stop. The tissue grasper 10 may also be pre-programmed to reduce the clamping pressure at a predetermined rate and automatically send the pressure reading to the computing device at the moment when perfusion through the grasped tissue restarts. The perfusion pressure reading may also be displayed on the display 20. This automated process eliminates human error in operating the tissue grasper 10 by controlling the amount of clamping pressure being applied to the tissue instead of the surgeon.

The tissue grasper 10 may also be used to determine the size of the staples to be used in stapling the bowel segments together. The staple size may be determined by viewing the third display section 20c of the tissue grasper 10, which indicates the thickness of the grasped tissue. The leg height of the staples selected for the stapling procedure will correspond to the thickness of the tissue. It is contemplated that the tissue thickness measured by the third sensors 42c, 44c may be sent to the computing device, which has stored therein a look-up table that contains a staple size corresponding to each tissue thickness measurement.

In addition to the thermographic endoscope 2 and the tissue grasper 10 being used to ensure that the tissue is in condition for reconnecting (e.g., stapling) or acceptable for reconnecting, the thermographic endoscope 2 and the tissue grasper 10 may also be used as a check after the staples have been fired to ensure that the tissue is healthy (e.g., has good blood flow, is healing properly, etc.).

The thermographic endoscope 2 and the tissue grasper 10 may also be configured to be incorporated into a robotic surgical system (not shown). The robotic surgical system is powered locally or remotely, and has electronic control systems localized in a console or distributed within or throughout the robotic surgical system. The robotic surgical system permits a surgeon to remotely manipulate the thermographic endoscope 2 and the tissue grasper 10 to more precisely control the movement thereof. The surgical system 1 may be configured to send the infrared images generated by thermographic endoscope 2 and the measurements gathered by the sensors 42a-c, 44a-c of tissue grasper 10 to an interface of the robotic surgical system on which the images and measurements may be displayed for the surgeon to read.

Although the illustrative embodiments of the present disclosure have been described herein, it is understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A method of determining viability of subject tissue, comprising:
    determining a local perfusion pressure of the subject tissue of a patient by applying pressure to the subject tissue using a tissue grasper;
    determining a systemic blood pressure of the patient;
    calculating a first index using the determined local perfusion pressure and the determined systemic blood pressure;
    reducing a temperature of the subject tissue from a baseline temperature to a temperature below the baseline temperature by contacting the subject tissue with pre-chilled tissue contacting surfaces of the tissue grasper;
    generating an infrared image of the subject tissue using a thermographic camera;
    analyzing the infrared image to determine a rate at which the subject tissue returns to the baseline temperature from the temperature below the baseline temperature; and
    determining viability of the subject tissue based on the first index and the determined rate.

2. The method according to claim 1, further comprising:
    assigning a numerical value to the subject tissue based on the determined rate; and
    comparing the numerical value to a known numerical value corresponding to viable tissue to determine the viability of the subject tissue.

3. The method according to claim 2, wherein determining the viability of the subject tissue further includes comparing the first index to a known first index corresponding to viable tissue.

4. The method according to claim 1, further comprising stapling the subject tissue upon determining that the subject tissue is viable.

5. The method according to claim 1, further comprising comparing the infrared image of the subject tissue with an infrared image of healthy tissue to determine whether the subject tissue exhibits normal blood flow characteristics.

6. The method according to claim 1, wherein the subject tissue is a pair of bowel segments.

7. The method according to claim 6, further comprising resecting a portion of at least one of the pair of bowel segments upon determining that the portion is not viable.

8. The method according to claim 7, further comprising stapling ends of the pair of bowel segments to reconnect the pair of bowel segments upon determining that the ends of the pair of bowel segments are viable.

9. The method according to claim 8, wherein determining that the ends of the pair of bowel segments are viable includes analyzing the infrared image to determine whether the ends of the pair of bowel segments exhibit normal heat distribution characteristics.

* * * * *